US008334387B2

(12) United States Patent
Whateley et al.

(10) Patent No.: US 8,334,387 B2
(45) Date of Patent: Dec. 18, 2012

(54) METHOD FOR MEASURING AROMATASE ACTIVITY

(75) Inventors: John Gerard Whateley, Maesteg (GB); Rahman Aziz Ismail, Cardiff (GB); Peter Gordon Laughton, Newport (GB)

(73) Assignee: GE Healthcare UK Limited, Little Chalfont (GB)

( * ) Notice: Subject to any disclaimer, the term of this patent is extended or adjusted under 35 U.S.C. 154(b) by 255 days.

(21) Appl. No.: 12/892,202

(22) Filed: Sep. 28, 2010

(65) Prior Publication Data

US 2011/0014641 A1    Jan. 20, 2011

Related U.S. Application Data

(62) Division of application No. 10/561,817, filed as application No. PCT/GB2004/003341 on Jul. 30, 2004, now Pat. No. 7,829,714.

(30) Foreign Application Priority Data

Jul. 30, 2003 (GB) .................................. 0317743.3

(51) Int. Cl.
*C07D 471/04* (2006.01)
*C12Q 1/25* (2006.01)

(52) U.S. Cl. ................. 546/57; 435/4; 435/7.21; 546/49
(58) Field of Classification Search .................... 546/57, 546/49; 435/4, 7.21
See application file for complete search history.

(56) References Cited

U.S. PATENT DOCUMENTS
6,207,404 B1    3/2001    Miller et al.

FOREIGN PATENT DOCUMENTS
| WO | WO 01/14361 | 3/2001 |
| WO | WO 02/099424 | 12/2002 |
| WO | WO 03/020294 | 3/2003 |

OTHER PUBLICATIONS

Stresser, D., et al., "A High-Throughput Screen to Identify Inhibitors of Aromatase (CYP19)", *Analytical Biochemistry*, vol. 284, No. 2, 2000, p. 427-430.
Crespi, C., et al., Analytical Biochemistry, 1997, 248(1), 188-190.

*Primary Examiner* — Charanjit Aulakh

(57) ABSTRACT

The present invention relates to compounds useful for measuring aromatase activity. The invention further provides methods for measuring aromatase activity and for screening test agents which modulate aromatase activity. A kit is also provided for use in such screening methods.

17 Claims, 5 Drawing Sheets

METHOD FOR MEASURING AROMATASE ACTIVITY

CROSS-REFERENCE TO RELATED APPLICATIONS

This application is a divisional of U.S. patent application Ser. No. 10/561,817 filed Dec. 7, 2006, which is a filing under 35 U.S.C. §371 and claims priority to international patent application number PCT/GB2004/003341 filed Jul. 30, 2004, published on Feb. 10, 2005 as WO 2005/012901, which claims priority to application number 0317743.3 filed in Great Britain on Jul. 30, 2003.

FIELD OF THE INVENTION

The present invention relates to compounds, methods and a kit for measuring aromatase activity. The invention can be used for determining both in vitro and in vivo enzyme activity and for identifying/characterising inhibitors.

BACKGROUND OF THE INVENTION

Assays for measuring enzyme activity are widely employed in the pharmaceutical and environmental sciences. With the advent of combinatorial chemistry and high throughput screening there is a growing need for simple, sensitive and cost-effective assays to screen for potential modulators of enzyme activity.

The enzyme aromatase cytochrome P450 19 A1 (EC 1.14.14.1) is the product of the CYP19 gene, a member of the P450 superfamily of genes. Aromatase catalyses the rate-limiting step in oestrogen biosynthesis, the conversion of $C_{19}$ androgenic steroids to the corresponding oestrogen (FIG. 1), a reaction termed aromatisation since it converts the $\Delta^4$-3-one ring of the androgen to the phenolic A-ring of oestrogen (Ciolino et al., 2000, *British Journal of Cancer*, 83, 333-337).

Oestrogens are the most important etiological factors in the growth and development of many breast carcinomas in both pre- and post-menopausal women. Breast tumours from post-menopausal women contain high levels of 17β-oestradiol despite the presence of low plasma 17β-oestradiol concentrations. It is now widely accepted that breast tumours can synthesise 17β-oestradiol from adrenal androgen precursors. Synthesis occurs through the aromitisation of androstenedione to oestrone by aromatase, followed by conversion of oestrone to 17β-oestradiol by 17β-hydroxysteroid dehydrogenase type 1 (James et al., 2001, *Endocrinology* 142, 1497-1505).

When measured in-vitro, aromatase activity was found to be higher in breast tumours than in adjacent or healthy fat cells. Furthermore, adipose stromal cells surrounding cancerous cells have been shown to contain higher levels of aromatase mRNA than corresponding cells in non-cancerous areas (Chen et al., 1999, *Endocrine-Related Cancer*, 6, 149-156). Thus aromatase activity in tumours or surrounding tissue is believed to play a significant role in promoting tumour growth due to local production of oestrogen.

Aromatase offers a key point of intervention in the treatment of breast cancer by reducing the activity and consequently the level of oestrogen synthesised at the site of the tumour. Thus aromatase inhibitors provide significant benefit to many breast cancer patients (James et al., 2001, *Endocrinology* 142, 1497-1505).

Aromatase is an important enzyme not only from a medical and pharmaceutical viewpoint in the treatment of breast cancer but also from an environmental perspective because inhibitors have been identified as potential environmental toxins, or so called 'endocrine disrupters' (Mak et al., 1999, *Environmental Health Perspectives*, 107, 855-860). The development of a simple, high throughput screening assay to identify modulators and particularly inhibitors of aromatase activity is thus of considerable commercial interest.

Fluorescence Detection Methods

Fluorescence-based assays offer significant advantages over radiochemical, ELISA, antibody and more traditional techniques for measuring enzyme activity in terms of simplicity of handling, sensitivity, cost and ease of automation. Recently there has been considerable interest in the application of fluorescence resonance energy transfer (FRET) assays which involve the use of substrates having donor and quenching acceptors on the same molecule. WO 94/28166, for example, reports the use of such FRET labels attached to a polypeptide substrate which fluoresce more intensely on hydrolysis by a protease.

While FRET techniques offer greater sensitivity and reliability for use in screening assays than simple fluorescent intensity techniques, the substrates are considerably more expensive to prepare and purify due to their complex nature. Thus the preparation of FRET labels is demanding in terms of both analytical and/or purification and material costs. Furthermore the only method for distinguishing conventional fluorescent or FRET labels is by their absorption and emission spectra.

Fluorescence lifetime measurements that may be utilised in the present invention offer significant advantages over conventional fluorescence techniques that are based solely on quantifying fluorescence intensity. Fluorescence lifetime is determined from the same spectrally resolved intensity signal, but is additionally resolved in the temporal domain. Fluorescence lifetime techniques provide greater discrimination because the signal is largely unaffected by 'background noise'. A further advantage with this technique is that several different events can be measured simultaneously by selecting labels having distinguishable lifetimes, thus enabling multiplexing. In addition, measurements of fluorescence lifetime are unaffected by concentration effects and photobleaching.

Aromatase Assays

Several assay formats have been reported for the measurement of aromatase activity. These can be divided into two categories depending on the use of a 'natural' or a surrogate substrate. Detection methodologies have included the use of radioisotopic tracers (e.g. Thompson & Siiteri, 1974, *Journal of Biological Chemistry*, 249, 5364-5372), fluorescence intensity (Crespi et al., *Analytical Biochemistry*, 1997, 248, 188-190), enzyme activity (e.g. Chabab et al., 1986, *Journal of Steroid Biochemistry*, 25, 165-169) and fast liquid chromatography (Fauss & Pyerin, 1993, *Analytical Biochemistry*, 210, 421-423).

Odum and Ashby (*Toxicology Letters* (2002), 129, 119-122) describe a radiometric assay for measuring aromatase activity using the 'tritiated water assay'. The assay quantifies enzyme activity based on the release of $^3H$ as $^3H_2O$ from the 1β position of the substrate during aromatisation. A final reaction contained rat ovary microsomes and an NADPH generating system together with the substrate 1β($^3H$)-androstenedione and potential aromatase inhibitors in dimethyl sulphoxide. Reactions were started by addition of the substrate and were carried out at 37° C. for 30 min. Reactions were stopped by addition of chloroform-methanol and the mixture shaken for 60 s. After removal of the solvent, a suspension of dextran-coated charcoal was added. The mixture was left for 1 h at 4° C., centrifuged and 500 μl of the supernatant added to scintillant and counted in a liquid scintillation counter.

Although this assay has been widely used in the literature (e.g. WO 03/045925) as a means for identifying potential inhibitors it is clearly not amenable to high throughput procedures as it is a labour intensive and time-consuming, requiring radiolabelled substrate.

Crespi et al. (*Analytical Biochemistry* (1997), 248, 188-190) describe a microtitre plate-based fluorimetric intensity assay that can be used to measure the activity of recombinant human aromatase expressed in insect cells and prepared as microsomes. The assay uses dibenzylfluorescein (DBF) as the substrate and reports a number of $IC_{50}$ values that are in many cases different from reported values. These differences are reportedly due to variation in methodology such as substrate choice and the use of cell based systems. The use of a 'surrogate' substrate in this second format may explain why the $IC_{50}$ differ from the published values.

There is therefore a continued need in the pharmaceutical and environmental sciences for improved fluorescence-based assays for measuring aromatase activity. Such assays may have one or more of the following attributes: homogeneity, high sensitivity, good reliability, robustness, simplicity of use, low cost, ease of automation, label specificity and/or more than one form of detection for distinguishing labelled compounds. Preferably the improved assays display more than one of these features and preferably they display all of these features. The present invention seeks to provide novel reagents and methods for performing such an assay.

SUMMARY OF THE INVENTION

According to a first aspect of the present invention, there is provided a compound of Formula I:

R-L-S        (I)

wherein R is a fluorescent dye molecule;
  L is an optional linkage group containing one or more atoms comprising hydrocarbon chains which may also contain other atoms such as N, O and S; and
  S is a molecule comprising a substrate group of the enzyme aromatase
characterised in that the fluorescence signal of said compound changes in respect of fluorescence intensity or fluorescence lifetime when the compound is acted upon by an enzyme with aromatase activity.

Suitably, R is selected from the group consisting of fluorescein, rhodamine, coumarin, BODIPY™ dye, phenoxazine, cyanine, Alexa FLUOR®, merocyanine, CY™3B, CY™5, CY™5.5, CY™7, acridone, quinacridone, and squarate dyes.

A range of fluorescent labels are commercially available which could be used as a fluorescent reporter moiety R in accordance with the present invention. Examples include, but are not limited to, oxazine (e.g. MR 121, JA 242, JA 243) and rhodamine derivatives (e.g. JA 165, JA 167, JA 169) as described in WO 02/081509. Other examples (as described in WO 02/056670) include, but are not limited to CY™5, CY™5.5 and CY™7 (GE Healthcare); merocyanine (Few Chemicals), IRD41 and IRD700 (Licor); NIR-1 and IC5-OSu (Dojindo); Alexa FLUOR® 660 & Alexa FLUOR® 680 (Molecular Probes); LaJolla Blue (Diatron); FAR-Blue, FAR-Green One & FAR-Green Two (Innosense); ADS 790-NS and ADS 821-NS (American Dye Source); indocyanine green (ICG) and its analogues (U.S. Pat. No. 5,968,479); indotricarbocyanine (ITC, WO 98/47538); fluorescent quantum dots (zinc sulfide-capped cadimium selenide nanocrystals—QuantumDot Corp.) and chelated lanthanide compounds (fluorescent lanthanide metals include europium and terbium).

Preferably, R is an acridone dye, as described in WO 02/099424, of formula II:

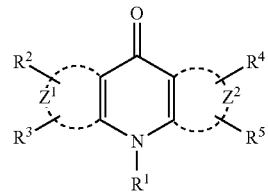

(II)

wherein:
groups $R^2$ and $R^3$ are attached to the $Z^1$ ring structure and groups $R^4$ and $R^5$ are attached to the $Z^2$ ring structure;
$Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;
$R^1$, $R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, $C_1$-$C_6$ alkoxy, aryl, heteroaryl, $C_1$-$C_{20}$ alkyl, aralkyl, the group -E-F where E is a spacer group having a chain from 1-60 atoms selected from the group consisting of carbon, nitrogen, oxygen, sulphur and phosphorus atoms and F is a target bonding group; and the group —$(CH_2$—$)_n$Y where Y is selected from sulphonate, sulphate, phosphonate, phosphate, quaternary ammonium and carboxyl and n is zero or an integer from 1 to 6.

Suitably, the target bonding group F is a reactive or functional group. A reactive group of the fluorescent dyes according to formula (II) can react under suitable conditions with a functional group of the substrate (i.e. group L or X); a functional group of a compound according to formula (II) can react under suitable conditions with a reactive group of the substrate. By virtue of these reactive and functional groups, the fluorescent dyes according to formula (II) may be reacted with and covalently bond to the substrate, such that the substrate becomes labelled with the fluorescent dye.

Preferably, when F is a reactive group, it is selected from the group consisting of succinimidyl ester, sulpho-succinimidyl ester, isothiocyanate, maleimide, haloacetamide, acid halide, vinylsulphone, dichlorotriazine, carbodiimide, hydrazide and phosphoramidite. Preferably, when F is a functional group, it is selected from hydroxy, amino, sulphydryl, imidazole, carbonyl including aldehyde and ketone, phosphate and thiophosphate.

Preferably, R is a quinacridone dye, as described in WO 02/099432, of Formula III:

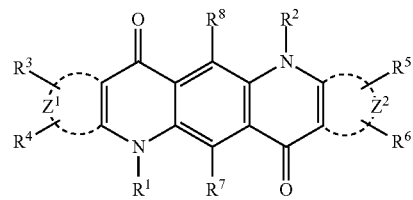

(III)

wherein:
groups $R^3$ and $R^4$ are attached to the $Z^1$ ring structure and groups $R^5$ and $R^6$ are attached to the $Z^2$ ring structure;
$Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;

$R^1$, $R^2$, $R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, aryl, heteroaryl, $C_1$-$C_{20}$ alkyl, aralkyl, the group -E-F where E is a spacer group having a chain from 1-60 atoms selected from the group consisting of carbon, nitrogen, oxygen, sulphur and phosphorus atoms and F is a target bonding group; and the group —$(CH_2—)_n$Y where Y is selected from sulphonate, sulphate, phosphonate, phosphate, quaternary ammonium and carboxyl and n is zero or an integer from 1 to 6.

Suitably, the target bonding group F is a reactive or functional group. A reactive group of the fluorescent dyes according to formula (III) can react under suitable conditions with a functional group of the substrate; a functional group of a compound according to formula (III) can react under suitable conditions with a reactive group of the substrate. By virtue of these reactive and functional groups, the fluorescent dyes according to formula (III) may be reacted with and covalently bond to the substrate, such that the substrate becomes labelled with the fluorescent dye.

Preferably, when F is a reactive group, it is selected from the group consisting of succinimidyl ester, sulpho-succinimidyl ester, isothiocyanate, maleimide, haloacetamide, acid halide, vinylsulphone, dichlorotriazine, carbodiimide, hydrazide and phosphoramidite. Preferably, when F is a functional group, it is selected from hydroxy, amino, sulphydryl, imidazole, carbonyl including aldehyde and ketone, phosphate and thiophosphate.

Preferred examples of acridone and quinacridone dyes (and their corresponding lifetimes (nano seconds)) are shown as compounds (IV), (V), (VI), (VII) and (VIII) in Table 1 as their NHS (N-hydroxysuccinimidyl)esters:

TABLE 1

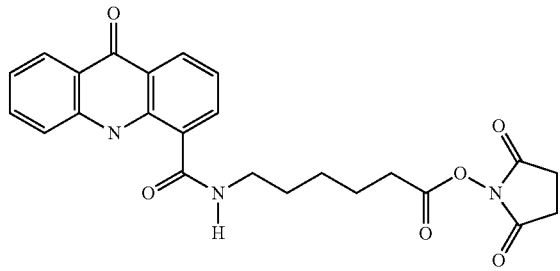

(IV) (4 nsec)

O-(N-Succinimidyl)-6-(9-oxo-9H-acridin-4-carboxamido)hexanoate (III)

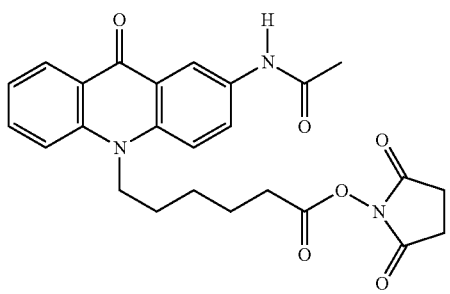

(V) (17 nsec)

O-(N-Succinimidyl)-6-(2-acetamido-9-oxo-9H-acridin-10-yl)hexanoate (IV)

TABLE 1-continued

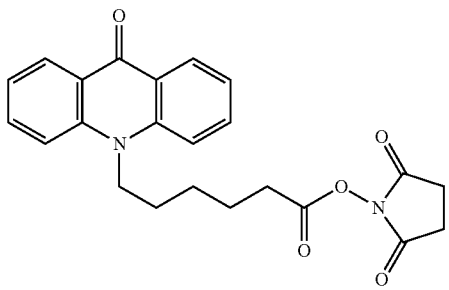

(VI) (14 nsec)

O-(N-Succinimidyl)-6-(9-oxo-9H-acridin-10-yl)hexanoate (V)

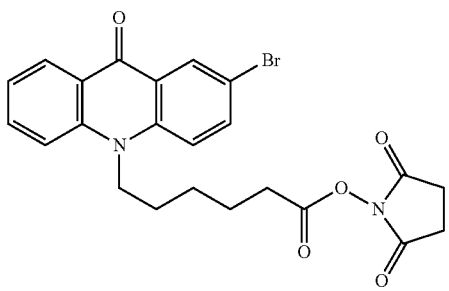

(VII) (8 nsec)

O-(N-Succinimidyl)-6-(2-bromo-9-oxo-9H-acridin-10-yl)hexanoate (VI)

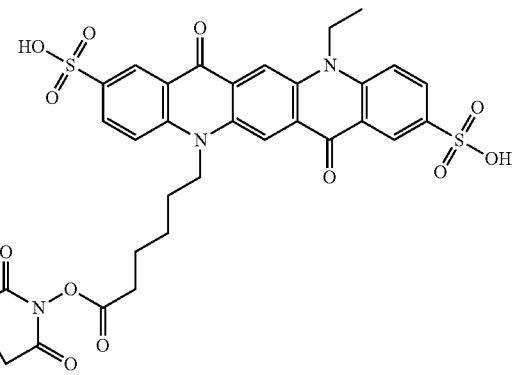

(VIII) (22 nsec)

6-(12-Ethyl-7,14-Dioxo-2,9-disulpho-7,14-dihydroquino[2,3-b]acridin-5(12H)-yl) hexanoic acid succinimidyl ester (VIII)

Suitably, L is a linker group containing from 1 to 40 linked atoms selected from carbon atoms which may optionally include one or more groups selected from —NR'—, —O—, —S—, —CH═CH—, —C≡C—, —CONH— and phenylenyl groups, wherein R' is selected from hydrogen and C1 to C4 alkyl.

Suitably, L is a linker group containing from 2 to 30 atoms, preferably from 6 to 20 atoms.

Preferably, L is a linker group selected from the group: {(—CHR'—)p-Q-(—CHR'—)r}s where each Q is selected from CHR', NR', O, —CH═CH—, Ar and —CONH—; each R' is independently hydrogen or C1 to C4 alkyl; each p is independently 0 to 5; each r is independently 0 to 5; and s is either 1 or 2. More preferably, Q is selected from the group consisting of —CHR'—, —O— and —CONH—, where R' is hydrogen or C1 to C4 alkyl.

Preferably, Group S is a steroid of Formula IX or a derivative thereof (IX)

wherein:
$R^1$ and $R^2$ are selected from H and methyl;
$R^3$ is selected from H, $C_1$-$C_8$ alkyl, cyano, —$(CH_2)_k$—$OR^a$; —$(CH_2)_k$—$COOR^a$; —$(CH_2)_k$—$SO_3R^a$; —$(CH_2)_k$—CHO, —$(CH_2)_k$—$NR^bR^c$ and —$(CH_2)_k$—$COR^d$;
$R^4$ is selected from H, —$COR^a$ and hydroxyl;
$R^5$ is selected from H, —$COR^a$, hydroxyl, cyano and halide;
$R^6$ is selected from H and hydroxyl;
$R^7$, $R^8$ and $R^9$ are independently selected from H, —$COR^a$ and hydroxyl;
$R^{10}$ is selected from H and halide; and
where $R^a$ is selected from H and C1-C4 alkyl, optionally substituted with OH; $R^b$ and $R^c$ are selected from H and $C_1$-$C_4$ alkyl;
$R^d$ is selected from $C_1$-$C_8$ alkyl or $C_1$-$C_8$ alkyl optionally substituted with $COOR^a$, OH, $OR^a$ or $SO_3R^a$;
and k is zero or an integer from 1 to 8.

Halogen and halide groups are selected from fluorine, chlorine, bromine and iodine.

Suitably, Group S is a steroid selected from the group of steroid families consisting of 4-androsten-3-one, 4-cholesten-3-one, 4-estren-3-one and 4-pregnen-3-one derivatives.

Preferably, Group S is androstenedione of Formula X or a derivative thereof (X)

Preferably, Group S is testosterone of Formula XI or a derivative thereof (XI)

In a preferred embodiment of the first aspect, there is provided a compound of Formula XII (XII)

In a second aspect of the present invention, there is provided a method for measuring aromatase activity in a sample, the method comprising the steps of:
i) measuring the fluorescence intensity or fluorescence lifetime of a compound according to any preceding claim prior to adding it to said sample;
ii) adding said compound to said sample under conditions which favour aromatase activity, and
iii) measuring a change in fluorescence intensity or fluorescence lifetime of said compound following step ii);
wherein said change in fluorescence intensity or fluorescence lifetime can be used to determine aromatase activity.

Suitably, the sample is selected from the group consisting of extract, cell, tissue and organism. The cell or organism may be naturally occurring or may be a recombinant cell or organism which has been genetically engineered to over-express a particular protein, such as aromatase.

In a third aspect of the present invention, there is provided a method of screening for a test agent whose effect upon the activity of aromatase is to be determined, said method comprising the steps of:
i) performing the method as hereinbefore described in the presence of said agent; and
ii) comparing the activity of said aromatase in the presence of the agent with a known value for the activity of aromatase in the absence of the agent;
wherein a difference between the activity of the aromatase in the presence of the agent and said known value in the absence of the agent is indicative of the effect of the test agent upon the activity of aromatase.

A test agent may be, for example, any organic or inorganic compound such as a synthetic molecule or a natural product (e.g. peptide, oligonucleotide), or may be an energy form (e.g. light or heat or other forms of electro magnetic radiation).

Suitably, the known value is stored upon an electronic database. Optionally, the value may be normalised (for example, to represent 100% aromatase activity) and compared to the normalised activity of the enzyme in the presence of the test agent. In this way, only test agents affecting enzyme activity by a certain minimum amount may be selected for further evaluation.

According to fourth aspect of the present invention, there is provided a method of screening for a test agent whose effect upon the activity of aromatase is to be determined, said method comprising the steps of:
i) performing the method of measuring aromatase activity as hereinbefore described in the presence and in the absence of the agent; and ii) determining the activity of said enzyme in the presence and in the absence of the agent;
wherein a difference between the activity of aromatase in the presence and in the absence of the agent is indicative of the effect of the test agent upon the activity of aromatase.

Suitably, the difference in activity between the activity of the enzyme in the absence and in the presence of the agent is normalised, stored electronically and compared with a value of a reference compound. Thus, for example, the difference in activity may be stored as a percentage inhibition (or percentage stimulation) on an electronic database and this value compared to the corresponding value for a standard inhibitor of aromatase. In this way, only test agents meeting a certain pre-determined threshold (e.g. as being as effective or more effective than the reference compound) may be selected as being of interest for further testing.

The assay method according to the present invention is preferably performed in the wells of a multiwell plate, e.g. a microtitre plate having 24, 96, 384 or higher densities of wells eg. 864 or 1536 wells. Alternatively, the assay may be conducted in assay tubes or in the microchannels of a multifluidic device or in a FACS machine. In a typical assay, a sample containing the substance of interest is mixed with the reaction mixture in a well. The reaction is initiated by the addition of enzyme. The reaction is allowed to proceed for a fixed time and stopped with a stop reagent (for example, EDTA).

The reaction mixture can be pre-dispensed into the wells of such a plate.

Typically, enzyme assays are performed under "stopped" conditions. By this it is meant that the reaction is allowed to proceed for a predetermined period and then terminated with a stop reagent. The nature of the stop reagent is typically a strong inhibitor of the enzyme and is often non-specific, for example, EDTA, is used to sequester metal ions that are normally present for enzyme activity. In embodiments of the second, third and fourth aspects, assays for aromatase activity either in the presence of or in the absence on a test compound, may be performed under continuous measurement. Because the fluorescence intensity and/or lifetime of the labelled substrate is monitored continuously and can be seen to change continuously, the labelled substrate does not need separation from the product of the enzymatic reaction. A time-course of the reaction may be obtained in this manner, thus allowing kinetic studies to be performed in real time.

In general the assay will consist of several components, typically the enzyme, substrate, cofactors, metal ions, buffer salts and possibly test or standard inhibitor compounds.

Additionally it may be necessary to run the assays in the presence of low percentages of organic solvents such as DMSO. In this invention it is possible to add any of the reagents to the mix whilst omitting a critical component in any order. This type of reaction can then be monitored for non-specific effects. It is also possible to construct mixture with no enzyme for further controls. Due to the nature of the reactions, it is then possible to add the final component and monitor changes either in real time or by stopping the reaction at some point in the future.

The methods of the invention can be carried out in samples derived from cells, tissues, organisms and extracts. Biological samples may, for example, be homogenates, lysates or extracts prepared from whole organisms, parts of an organism or tissues. For example, the assay can be conducted on a variety of body fluids such as blood, mucus, lymphatic fluid, synovial fluid, cerebrospinal fluid, saliva, amniotic fluid, urine, vaginal fluid and semen. In particular, the assay may be conducted on adipose or breast tissues and cells.

Furthermore, it is possible to conduct the assay in media, such as nutrient broth or similar media, where it is possible to grow either eukaroytic or prokaryotic cells. Cells engineered to over-express aromatase, such as JEG3 choriocarcinoma cells obtained from ATCC (Bhatnager et al., 2001, *Journal of Steroid Biochemistry and Molecular Biology,* 76, 199-202) are particularly useful for screening inhibitors.

Suitably, conventional detection methods can be employed to measure fluorescence intensity and/or the lifetime of the label. These methods include instruments using photo-multiplier tubes as detection devices. Several approaches are possible using these methods; e.g.

i) methods based upon time correlated single photon counting (cf. Principles of
Fluorescence Spectroscopy, (Chapter4) ed. J R Lakowicz, Second Edition, 1999, Kluwer/Academic Press)
ii) methods based upon frequency domain/phase modulation (cf. Principles of Fluorescence Spectroscopy, (Chapter5) ed. J R Lakowicz, Second Edition, 1999, Kluwer/Academic Press)
iii) methods based upon time gating (cf. Sanders et al., (1995) Analytical Biochemistry, 227 (2), 302-308).

Measurement of fluorescent intensity may be performed by means of a charge coupled device (CCD) imager, such as a scanning imager or an area imager, to image all of the wells of a multiwell plate. The LEADSEEKER™ (GE Healthcare) system features a CCD camera allowing imaging of high density microtitre plates in a single pass. Imaging is quantitative and rapid, and instrumentation suitable for imaging applications can now simultaneously image the whole of a multiwell plate.

According to a fifth aspect of the present invention, there is provided a method for measuring the distribution of a compound as hereinbefore described within a tissue, wherein the compound is capable of being taken up by a living cell within the tissue, the method comprising the steps of:
i) measuring the fluorescence intensity or fluorescence lifetime of the compound in a cell-free environment or a parental host cell;
ii) adding the compound to one or more cells or a cell engineered to over-express aromatase, and
iii) measuring the fluorescence intensity or lifetime of the compound following step ii);
wherein a change in fluorescence intensity or fluorescence lifetime indicates aromatase activity and can be used to determine the distribution of the compound. It will be understood that cells which have been genetically engineered to over-express aromatase compared to their parental host cells will exhibit significantly higher levels of enzyme activity.

Suitably, the distribution of the compound within the tissue of a first subject is compared with the distribution of the compound within the tissue of a second subject.

Suitably, the subject is selected from the group consisting of mammal, plant, insect, fish, bird, fly, nematode and algae. Preferably, the mammal is a mouse or a rat.

In a sixth aspect of the present invention, there is provided the use of a compound as hereinbefore described for measuring aromatase activity as an in vitro or an in vivo imaging probe.

In a seventh aspect of the present invention, there is provided a method of diagnosing a disease caused by an increase in aromatase activity in a subject using the method as hereinbefore described, comprising comparing the activity of aromatase in a sample taken from a first subject with the activity in a sample taken from a second healthy control subject, wherein any increase in activity measured in the sample taken from the first subject relative to the second healthy control subject is indicative of disease.

In a seventh aspect of the present invention, there is provided a kit comprising:

i) a compound as hereinbefore described; and
ii) an assay buffer; and optionally
iii) a stop buffer.

DETAILED DESCRIPTION OF THE INVENTION

Figure 1:
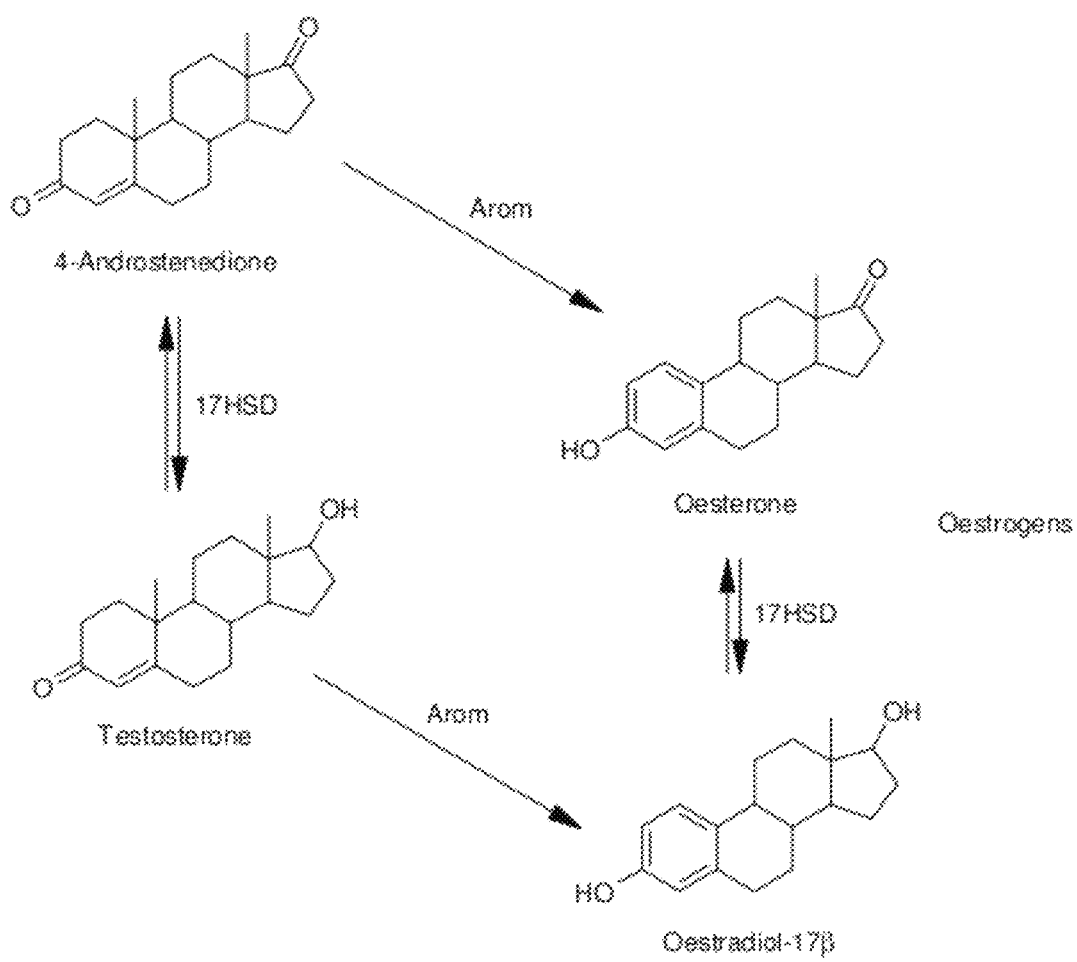
FIG. 1 illustrates the biochemical activity of aromatase in converting androstenedione to oestrone.

Synthesis of Aromatase Substrate i) Tert-Butyl 2-{[(3-oxoandrost-4-en-17-yl)carbonyl]amino}-ethylcarbamate

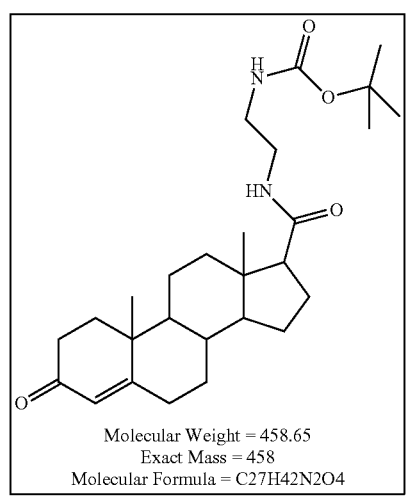

Formula (XIII)

Molecular Weight = 458.65
Exact Mass = 458
Molecular Formula = C27H42N2O4

To 0.49 g of 4-androsten-3-one-17β-carboxylic acid was added N,N-dimethylformamide (3 ml), N,N-diisopropylethylamine (0.55 ml) and O—(N-Succinimidyl)-N,N,N',N'-tetramethyluronium tetrafluoroborate (0.48 g). On stirring at room temperature (under an atmosphere of nitrogen) for 1.5 hours tert Butyl N-(2-aminoethyl)carbamate (0.25 g) was added. The mixture was stirred at room temperature for 3 days after which time the volatile components were removed on a rotary evaporator. Flash column chromatography was performed and the relevant fractions combined and stripped of solvent using a rotary evaporator. This gave 0.50 g of the desired material (Formula XIII).

Mass spectrum: 459.30 (M+H)

ii) N-(2-aminoethyl)-3-oxoandrost-4-ene-17-carboxamide

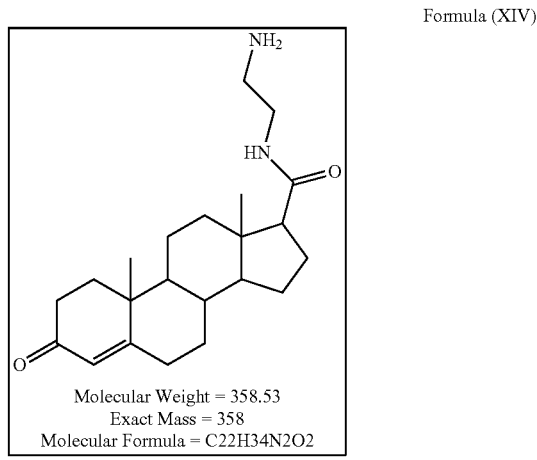

Formula (XIV)

Molecular Weight = 358.53
Exact Mass = 358
Molecular Formula = C22H34N2O2

To 16.5 mg of Tert-Butyl 2-{[(3-oxoandrost-4-en-17-yl)carbonyl]amino}-ethylcarbamate was added 0.5 ml of 95% trifluoroacacetic acid/water. On standing for 2 hours the volatile components were removed using a rotary evaporator. The resulting product (Formula XIV), which was an oil, was used without further purification. Mass spectrum: 359.23 (M+H)

iii) N-(2-{[2-(6,7,8,9,10-tetrahydro-14-sulfonato-16,16,18,18-tetramethyl-7aH-bisindolinium[3,2-a,3',2'-a]pyrano[3,2-c,5,6-c]dipyridin-5-ium)acetyl]amino}ethyl)-3-oxoandrost-4-ene-17-carboxamide

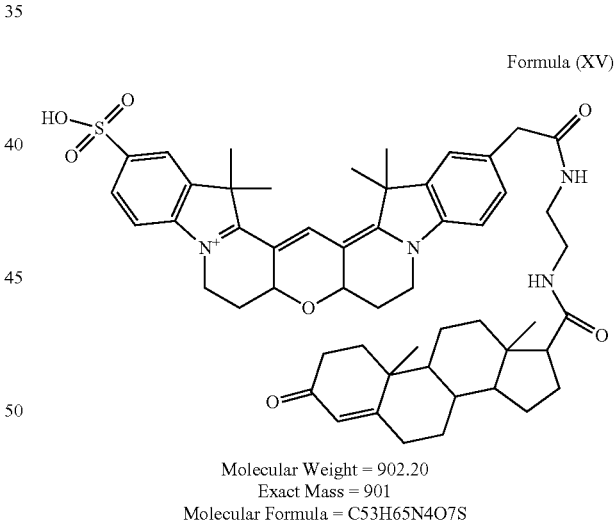

Formula (XV)

Molecular Weight = 902.20
Exact Mass = 901
Molecular Formula = C53H65N4O7S

To 6,7,8,9,10-tetrahydro-2-carboxymethyl-14-sulfonato-16,16,18,18-tetramethyl-7aH-bisindolinium[3,2-a,3',2'-a]pyrano[3,2-c,5,6-c]dipyridin-5-ium NHS ester (1.0 mg) was added N-(2-aminoethyl)-3-oxoandrost-4-ene-17-carboxamide (0.6 mg), diisopropylethylamine (0.01 ml) and dichloromethane (0.2 ml). This mixture was placed on a roller for 18 hours and then purified by preparatory HPLC [column: Phenomenex JUPITER™ 10u C18 300A 250×21.2 mm. Method: 20 ml/min, 5% to 50% B over 30 min (A=water 0.1% TFA, B=CH3CN 0.1% TFA). Peaks were detected at 559 nm. RT (product) ~27 min]. Relevant fractions were combined and concentrated on a rotary evaporator. The material was then freeze dried to give 1.0 mg of the desired product (Formula XV). Mass spectrum: 902 (M+H)

iv) Ethyl 6-(9-oxoacridin-10(9H)-yl)hexanoate

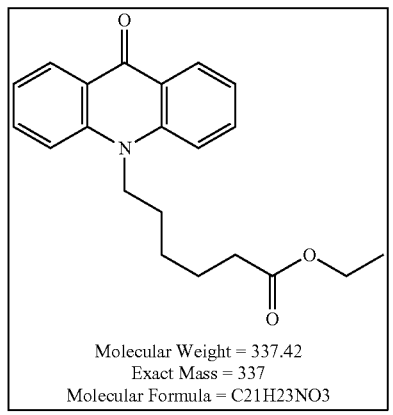

Formula (XVI)

Molecular Weight = 337.42
Exact Mass = 337
Molecular Formula = C21H23NO3

To 9(10H)-acridone (1.0 g) was added tetrahydrofuran (15 ml) under an atmosphere of nitrogen. Sodium hydride (0.25 g) was added with stirring; after 30 minutes ethyl 6-bromohexanoate (1.12 ml) was added and the mixture heated to reflux for 18 hours. After this time water (10 ml) was added and the layers separated. The organic layer was dried over magnesium sulfate, filtered and evaporated to dryness. Dry flash column chromatography was performed to give 0.85 g of the required material (Formula XVI). Mass spectrum: 338 (M+H).

v) 6-(9-oxoacridin-10(9H)-yl)hexanoic acid

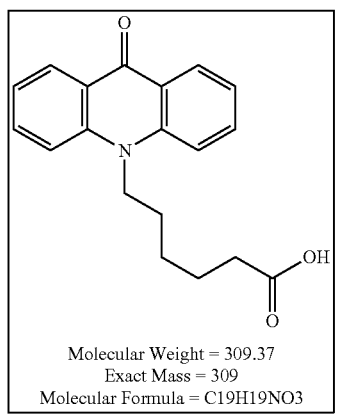

Formula (XVII)

Molecular Weight = 309.37
Exact Mass = 309
Molecular Formula = C19H19NO3

To ethyl 6-(9-oxoacridin-10(9H)-yl)hexanoate (0.80 g) was added acetic acid (9 ml) and 2M hydrochloric acid (2.5 ml). The mixture was heated to 100° C. for 18 hours after which time the volatile components were removed on a rotary evaporator. Diethyl ether was added (25 ml) and the mixture stirred for 15 minutes. The resulting material was filtered off and air dried to give 0.36 g final product (Formula XVII). Mass spectrum: 310 (M+H).

vi) Tert-Butyl 2-{[6-(9-oxoacridin-10(9H)-yl)hexanoyl]amino}ethylcarbamate

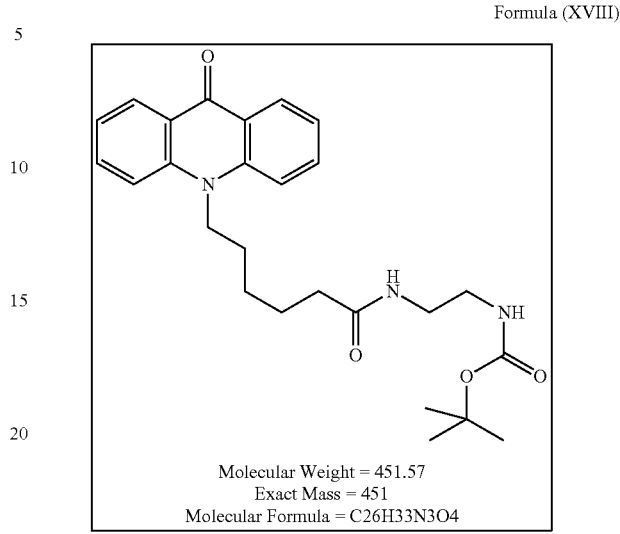

Formula (XVIII)

Molecular Weight = 451.57
Exact Mass = 451
Molecular Formula = C26H33N3O4

To 0.48 g of 6-(9-oxoacridin-10(9H)-yl)hexanoic acid was added dichloromethane (6 ml) and thionyl chloride (0.2 ml). This mixture was heated to reflux for 1 hour after which time the volatile components were removed by application of vacuum. To the resulting oil was added dichloromethane (3 ml), pyridine (3 ml) and t-butyl N-(2-aminoethyl)carbamate (250 mg). This mixture was stirred for 18 hours after which time it was poured into 0.5M sodium hydroxide solution (15 ml) and extracted with dichloromethane (2×10 ml). The combined dichloromethane solutions were washed with 0.1M hydrochloric acid solution, dried over magnsium sulfate, filtered and evaporated to dryness. The resulting material was purified by column chromatography to give 0.30 g of a solid final product (Formula XVIII).

vii) N-(2-aminoethyl)-6-(9-oxoacridin-10(9H)-yl)hexanamide hydrochloride

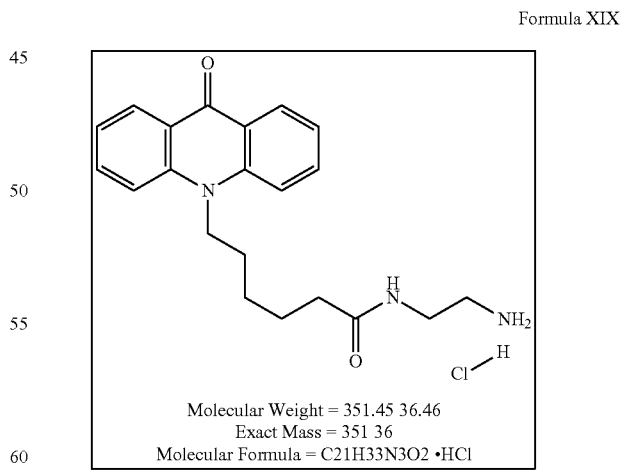

Formula XIX

Molecular Weight = 351.45 36.46
Exact Mass = 351 36
Molecular Formula = C21H33N3O2 •HCl To 0.30 g of tert-butyl 2-{[6-(9-oxoacridin-10(9H)-yl)hexanoyl]amino}ethylcarbamate was added dicholoromethane (DCM; 30 ml). HCl (g) was bubbled through the solution for 10 minutes. After this time the mixture was filtered and washed with DCM (3×20 ml) to give the desired product (0.15 g; Formula XIX). Mass spectrum: 352 (M+H).

viii) 3-oxo-N-(2-{[6-(9-oxoacridin-10(9H)-yl)hexanoyl]amino}ethyl)androst-4-ene-17-carboxamide Formula XX

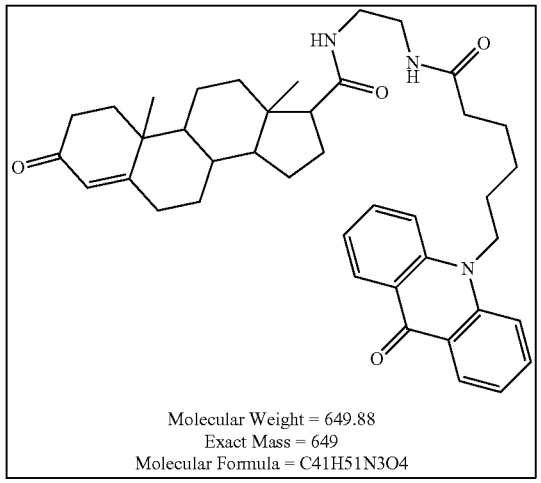

Molecular Weight = 649.88
Exact Mass = 649
Molecular Formula = C41H51N3O4

To 0.082 g of 4-androsten-3-one-17B carboxylic acid was added DMF (5 ml), DIPEA (0.045 ml) and O—(N-Succinimidyl)-N,N,N',N'-tetramethyluronium tetrafluoroborate (0.08 g). After stirring for 1 hour N-(2-aminoethyl)-6-(9-oxoacridin-10(9H)-yl)hexanamide hydrochloride (compound XVII) (0.10 g) was added and stirring continued for 3 days. Preparatory HPLC was performed [column: Phenomenex JUPITER™ 10u C18 300A 250×21.2 mm; 20 ml/min, 5% to 95% B over 30 min (A=water 0.1% TFA, B=CH3CN 0.1% TFA). Peaks were detected at 280 nm. RT (product) ~23 min] and the relevant fractions combined and concentrated on a rotary evaporator. Freeze drying gave 0.0683 g of product (Formula XX). Mass spectrum: 650 (M+H).

ix) 5-ethyl-7,14-dioxo-12-{6-oxo-6-[(2-{[(3-oxoandrost-4-en-17-yl) carbonyl]amino}ethyl)amino]hexyl}-5,7,12,14-tetrahydroquino[2,3-b]acridin-2,9-disulfonic acid Formula XXI

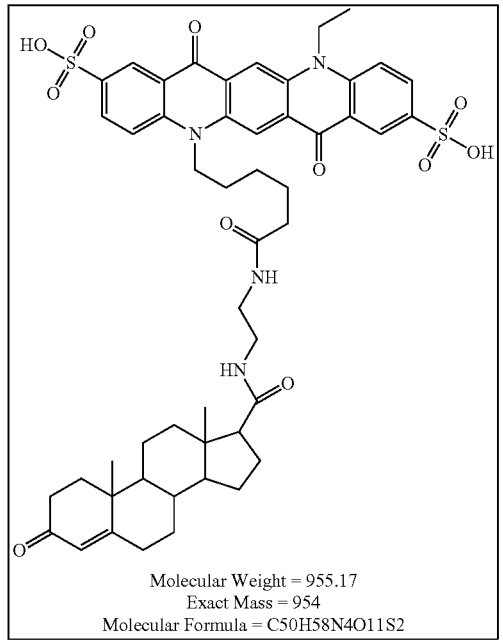

Molecular Weight = 955.17
Exact Mass = 954
Molecular Formula = C50H58N4O11S2

N-(2-aminoethyl)-3-oxoandrost-4-ene-17-carboxamide (1.0 mg) was dissolved in dichloromethane (1 ml) and a solution of 5-{6-[(2,5-dioxopyrrolidin-1-yl)oxy]-6-oxohexyl}-12-ethyl-7,14-dioxo-5,7,12,14-tetrahydroquino[2,3-b]acridin-2,9-disulfonic acid (2 mg) in DMF (1 ml) added. DIPEA (0.02 ml) was added and the mixture stirred at room temperature for 1 hour. After this time preparatory HPLC was performed to give 1.6 mg of the desired material (Formula XXI). Mass spectrum: 956 (M+H).

Aromatase Assay

NADPH was prepared to a final concentration of 1 mM in 100 mM disodium hydrogen phosphate buffer pH7.4. The labelled substrate (i.e. 3-oxo-N-(2-{[6-(9-oxoacridin-10 (9H)-yl)hexanoyl]amino}ethyl)androst-4-ene-17-carboxamide; Formula XIX) or chromophore alone (6-(9-oxoacridin-10(9H)-yl)hexanoic acid—compound XVI) was added to the solution of NADPH to a final concentration of 2 µM.

100 µl of this reagent was dispensed in to replicate wells of a 96 well microtitre plate. To each well was dispensed 20 µ-30 µl of either the CYP19 (aromatase) containing microsomes or control microsomes (no CYP19). All microsomes were adjusted to the same protein concentration with assay buffer. The plates were incubated at 37° C. for 1 hour and then fluorescence intensity measurements were recorded on the Envision Plate Reader (Perkin Elmer, US), excitation 405 nm/emission BFP450 nm.

Figure 2:
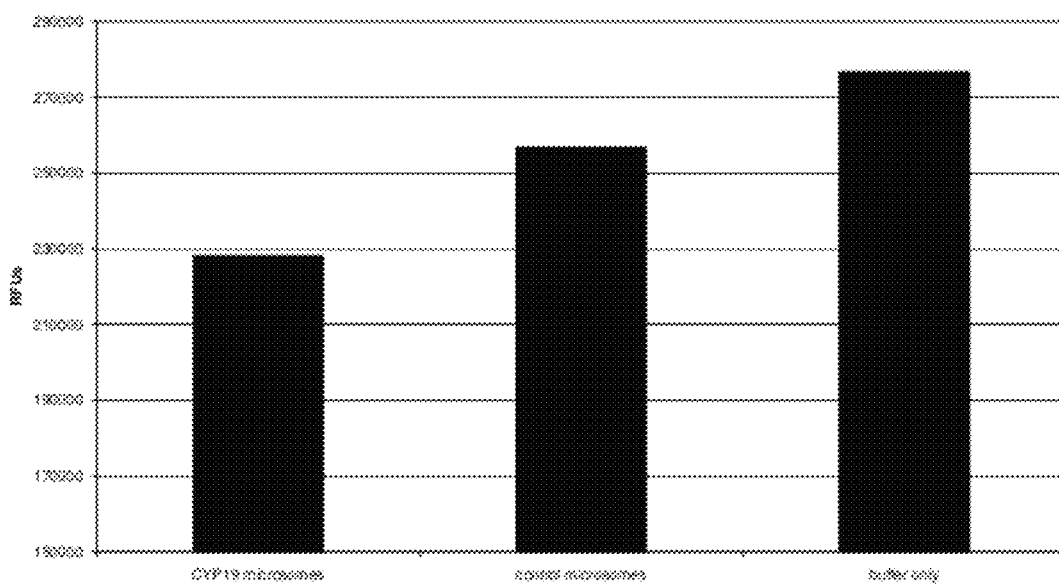
FIG. 2 shows a comparison of buffer only, control and CYP19 microsomes on fluorescence assay signal.

FIG. 2 compares the fluorescence intensity data from a 'buffer only' treatement and microsomes with and without aromatase activity. As can be seen, microsomes containing active aromatase produce a greater decrease in fluorescence intensity compared to the corresponding control microsome preparation. The decrease in signal in the presence of microsomes may represent quenching of the substrate signal due to the presence of protein/lipid.

Figure 3:
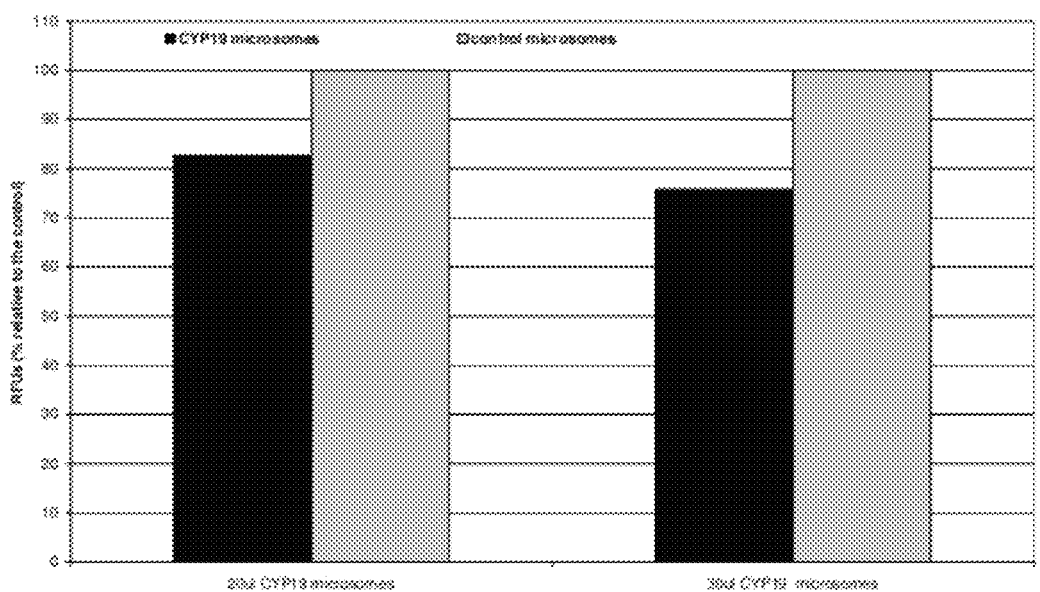
FIG. 3 depicts the effect that microsome volume has on fluorescence assay signal.

The fluorescence signal was seen to be proportional to the amount of enzyme/microsome present in the assay. FIG. 3 depicts the effect of microsome volume on the assay signal. A microsome volume of 20 µl generated a 17.5% decrease in intensity relative to the control reaction. This was further increased to 24.2% in the presence of 30 µl of microsome preparation.

Figure 4:
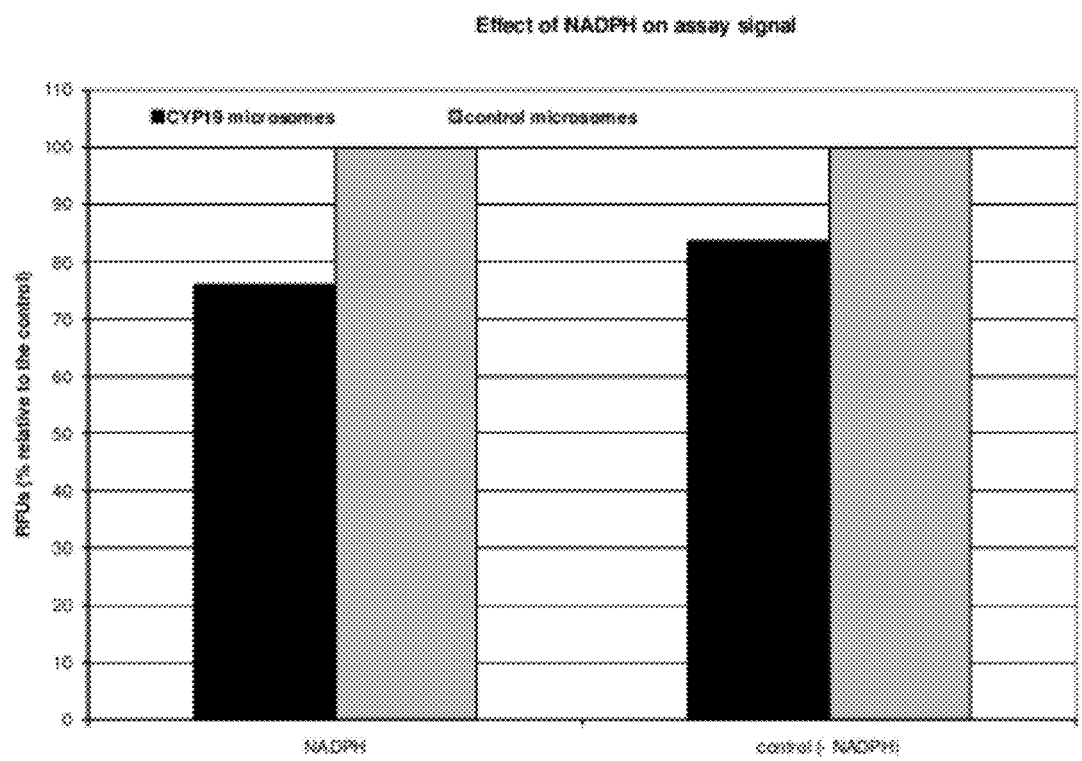
FIG. 4 illustrates the NADPH dependence of the microsome preparation (CYP19)/aromatase enzyme activity.

FIG. 4 illustrates the NADPH dependence of aromatase (CYP19 in the diagram) activity. A 24% decrease in fluorescence was observed in the presence of additional NADPH. This compared to 16% in the absence of additional co-factor. The signal observed in the absence of additional NADPH may reflect the presence of NAD(P)H in the enzyme preparation.

Figure 5:
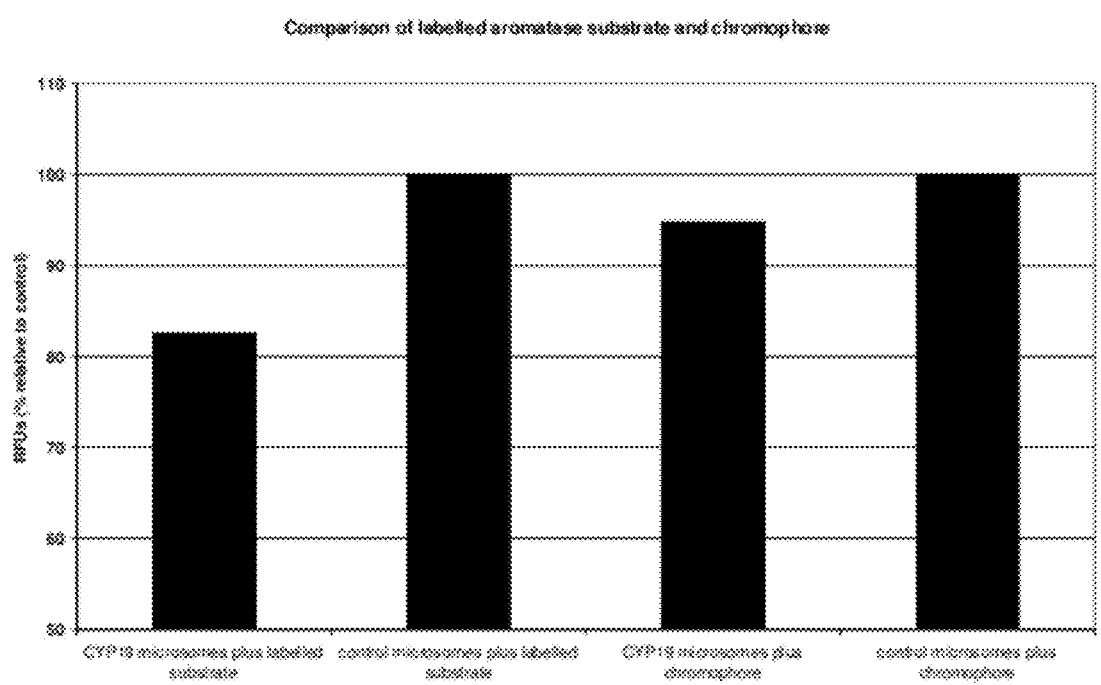
FIG. 5 shows the specificity of the aromatase enzyme for its substrate.

FIG. 5 shows the specificity of the enzyme for its substrate. In the presence of 20 µl of CYP19 aromatase preparation a 17.5% change in intensity relative to the control was observed for the labelled steroid reporter. The chromophore alone (i.e. 6-(9-oxoacridin-10(9H)-yl)hexanoic acid—compound XVII) generated a 5% change in intensity when incubated with CYP19 microsomes. Therefore, the observed decrease in fluorescence intensity was not due to the enzyme acting directly on the chromophore.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A compound having the structure shown in Formula 1:

R-L-S    (I)

wherein
R is a quinacridone dye of Formula III;

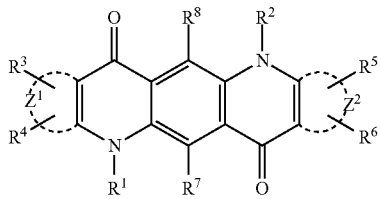

(III)

wherein:
groups $R^3$ and $R^4$ are attached to the $Z^1$ ring structure and groups $R^5$ and $R^6$ are attached to the $Z^2$ ring structure;
$Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;
$R^1$, $R^2$, $R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, aryl, heteroaryl, $C_1$-$C_{20}$ alkyl, aralkyl; the group -E-F where E is a spacer group having a chain from 1-60 atoms selected from the group consisting of carbon, nitrogen, oxygen, sulphur and phosphorus atoms and F is a target bonding group; and the group —$(CH_2$—$)_n$ Y where Y is selected from sulphonate, sulphate, phosphonate, phosphate, quaternary ammonium and carboxyl and n is zero or an integer from 1 to 6;
L is an optional linkage group containing from 2 to 30 atoms comprising hydrocarbon chains which may also contain other atoms such as N, O and S; and
S is a substrate group of the enzyme aromatase of formula IX

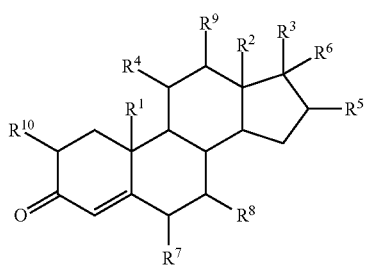

(IX)

wherein:
$R^1$ and $R^2$ are selected from H and methyl;
$R^3$ is selected from H, $C_1$-$C_8$ alkyl, cyano, —$(CH_2)_k$—$OR^a$; —$(CH_2)_k$—$COOR^a$; —$(CH_2)_k$—$SO_3R^a$; —$(CH_2)_k$—CHO, —$(CH_2)_k$—$NR^bR^c$ and —$(CH_2)_k$—$COR^d$;
$R^4$ is selected from H, —$COR^a$ and hydroxyl;
$R^5$ is selected from H, —$COR^a$, hydroxyl, cyano and halide;
$R^6$ is selected from H and hydroxyl;
$R^7$, $R^8$ and $R^9$ are independently selected from H, —$COR^a$ and hydroxyl;
$R^{10}$ is selected from H and halide; and
where $R^a$ is selected from H and C1-C4 alkyl, optionally substituted with OH; $R^b$ and $R^c$ are selected from H and $C_1$-$C_4$ alkyl;
$R^d$ is selected from $C_1$-$C_8$ alkyl or $C_1$-$C_8$ alkyl optionally substituted with $COOR^a$, OH, $OR^a$ or $SO_3R^a$;
and k is zero or an integer from 1 to 8;
and further wherein the fluorescence signal of said compound changes in respect of fluorescence lifetime when the compound is acted upon in vitro or in vivo by an enzyme with aromatase activity.

2. The compound of claim 1, wherein L is a linker group containing from 6 to 20 atoms.

3. The compound of claim 1, wherein L is a linker group selected from the group: $\{(-CHR'-)_p-Q-(-CHR'-)_r\}_s$
where each Q is selected from CHR', NR', O, —CH=CH—, Ar and —CONH—;
each R' is independently hydrogen or $C_1$ to $C_4$ alkyl;
each p is independently 0 to 5;
each r is independently 0 to 5;
and s is either 1 or 2.

4. The compound of claim 3,
wherein Q is selected from the group consisting of —CHR'—, —O— and —CONH—, where R' is hydrogen or $C_1$ to $C_4$ alkyl.

5. The compound of claim 1, wherein Group S is a steroid selected from the group of steroid families consisting of 4-androsten-3-one, 4-cholesten-3-one, 4-estren-3-one and 4-pregnen-3-one derivatives.

6. A method for measuring aromatase activity in a sample, the method comprising the steps of:
   i) measuring the fluorescence lifetime of the compound of claim 1 prior to adding it to said sample;
   ii) adding said compound to said sample under conditions which favour aromatase activity; and
   iii) measuring a change in fluorescence lifetime of said compound following step ii);
   wherein said change in fluorescence lifetime can be used to determine aromatase activity.

7. The method of claim 6, wherein the sample is selected from the group consisting of extract, cell, tissue and organism.

8. A method of screening for a test agent whose effect upon the activity of aromatase is to be determined, said method comprising the steps of:
   i) performing the method of claim 6 in the presence of said agent; and
   ii) comparing the activity of said aromatase in the presence of the agent with a known value for the activity of aromatase in the absence of the agent;
   wherein a difference between the activity of the aromatase in the presence of the agent and said known value in the absence of the agent is indicative of the effect of the test agent upon the activity of aromatase.

9. The method of claim 8, wherein the known value is stored upon an electronic database.

10. A method of screening for a test agent whose effect upon the activity of aromatase is to be determined, said method comprising the steps of:
   i) performing the method of claim 8 in the presence and in the absence of the agent; and
   ii) determining the activity of said enzyme in the presence and in the absence of the agent;

wherein a difference between the activity of aromatase in the presence and in the absence of the agent is indicative of the effect of the test agent upon the activity of aromatase.

11. The method of claim 9, wherein said difference in activity between the activity of aromatase in the absence and in the presence of the agent is normalised, stored electronically and compared with a value of a reference compound.

12. A method for measuring the distribution of the compound of claim 1 within a tissue, wherein the compound is capable of being taken up by a living cell within said tissue, the method comprising the steps of:
   i) measuring the fluorescence lifetime of the compound in a cell-free environment or a parental host cell;
   ii) adding the compound to one or more cells or a cell engineered to over-express aromatase, and
   iii) measuring the fluorescence lifetime of the compound following step ii);
   wherein a change in fluorescence lifetime indicates aromatase activity and can be used to determine the distribution of the compound.

13. The method of claim 12, wherein the distribution of the compound within the tissue of a first subject is compared with the distribution of the compound within the tissue of a second subject.

14. The method of claim 13, wherein said subject is selected from the group consisting of mammal, plant, insect, fish, bird, fly, nematode and algae.

15. The method of claim 14, wherein the mammal is a mouse or a rat.

16. A method of diagnosing a disease caused by an increase in aromatase activity in a subject using the method of claim 6, comprising comparing the activity of aromatase in a sample taken from a first subject with the activity in a sample taken from a second healthy control subject, wherein any increase in activity measured in the sample taken from the first subject relative to the second healthy control subject is indicative of disease.

17. A kit comprising:
   i) the compound of claim 1;
   ii) an assay buffer; and optionally
   iii) a stop buffer.

* * * * *